United States Patent
Schwint et al.

(10) Patent No.: US 7,964,765 B2
(45) Date of Patent: Jun. 21, 2011

(54) STYRENE MONOMER PROCESS BASED ON OXIDATIVE DEHYDROGENATION OF ETHYLBENZENE USING $CO_2$ AS A SOFT OXIDANT

(75) Inventors: Kevin J. Schwint, Long Valley, NJ (US); Richard J. Wilcox, West Caldwell, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 399 days.

(21) Appl. No.: 12/139,455

(22) Filed: Jun. 14, 2008

(65) Prior Publication Data
US 2009/0312589 A1    Dec. 17, 2009

(51) Int. Cl.
*C07C 5/327* (2006.01)

(52) U.S. Cl. ..................................... 585/441; 585/440

(58) Field of Classification Search .................. 585/441, 585/440
See application file for complete search history.

(56) References Cited

U.S. PATENT DOCUMENTS

| | | | |
|---|---|---|---|
| 4,021,500 | A | 5/1977 | Rogers |
| 4,788,371 | A | 11/1988 | Imai et al. |
| 5,053,572 | A | 10/1991 | Kim et al. |
| 5,324,702 | A | 6/1994 | Yoo et al. |
| 6,034,032 | A | 3/2000 | Park et al. |
| 6,037,511 | A | 3/2000 | Park et al. |
| 6,958,427 | B2 | 10/2005 | Park et al. |
| 2003/0166984 | A1 | 9/2003 | Park et al. |
| 2004/0181083 | A1 | 9/2004 | Proll et al. |
| 2007/0225532 | A1 | 9/2007 | Tonkovich et al. |
| 2008/0097133 | A1 | 4/2008 | Crone et al. |

FOREIGN PATENT DOCUMENTS

| | | |
|---|---|---|
| EP | 482276 A1 | 4/1992 |
| JP | 2002265396 | 9/2002 |

OTHER PUBLICATIONS

Notification Concerning Transmittal of International Preliminary Report on Patentability issued Dec. 18, 2010 by the International Bureau of WIPO in corresponding PCT Application No. PCT/US2009/047195 (8 pages).
International Search Report, Jul. 17, 2009.
J. Matsui, T. Sodesawa, F. Nozaki, "Influence of carbon dioxide addition upon decay of activity of a potassium-promoted iron oxide . . ." Applied Catalysis (1991), 67(2), 179-88.
S. Wang, Z.H. Zhu, "Catalytic Conversion of Alkanes and Olefins by Carbon Dioxide Oxidative Dehydrogenation . . . ", Energy and Fuels 18(2004), 1126-1139.
M.C. Chon, "Transformation of the old process: ethylbenzene to styrene with CO2 dilution", presentation at CHEMRAWN XVI Conference, (2003) Ottawa, Canada.
Sang-Eon Park, Jin S. Yoo, "New CO2 chenistry—Recent advances in utilizing CO2 as an oxidant and current understanding . . . ", Stud. Surf. Sci. Catal. 153 (2004), 303-314.

(Continued)

*Primary Examiner* — Thuan Dinh Dang
(74) *Attorney, Agent, or Firm* — Osha • Liang LLP

(57) ABSTRACT

Processes are provided for the production of styrene monomer by oxidative dehydrogenation of EB using $CO_2$ as a soft oxidant. Carbon dioxide is used as the reaction diluent in one or more dehydrogenation reactors and to supply the heat required for the endothermic reaction of EB to styrene monomer. In the dehydrogenation reactors, two parallel reactions for styrene monomer formation occur simultaneously: (1) direct EB dehydrogenation to styrene monomer over a catalyst using heat provided by the carbon dioxide, and (2) oxidative dehydrogenation of EB with carbon dioxide to form styrene monomer.

15 Claims, 3 Drawing Sheets

OTHER PUBLICATIONS

Naoki Mimura, Masahiro Saito, "Dehydrogenation of ethylbenzene to styrene over $Fe_2O_3/Al_2O_3$ catalysts in the presence of carbon dioxide", Catalysis Today 55 (2000), 173-178.

Do-Young Hong, et al., "Effect of carbon dioxide as oxidant in dehydrogenation of ethylbenzene to styrene over alumina-supported vanadium . . . " Catalysis Today 112(2006), 86-88.

Yoshihiko Ohishi, et al., "Dehydrogenation of ethylbenzene with $CO_2$ over Cr-MCM-41 catalyst", J. Mol. Catal. A: Chemical 230 (2005), 49-58.

I.P. Belomestnykh, et al., "New preparation methods of multicomponent vanadium oxide . . . ", Stud. Surf. Sci. Catal. (1992), 72 (New Dev. Sel. Oxid. Heterog. Catal.), 453-60.

F. Cavani, F. Trifiro, "Alternative processes for the production of styrene", Applied Catalysis A: General 133 (1995), 219-239.

STYRENE MONOMER PROCESS BASED ON OXIDATIVE DEHYDROGENATION OF ETHYLBENZENE USING $CO_2$ AS A SOFT OXIDANT

FIELD OF THE INVENTION

The present invention relates to processes for the dehydrogenation of a functionally substituted aliphatic compound to form a functionally substituted aliphatic compound comprised of carbon-carbon double or triple bonds using recycled carbon dioxide as an oxidant. In one embodiment, the process is used for producing styrene monomer by oxidative dehydrogenation of ethylbenzene using carbon dioxide as an oxidant.

BACKGROUND OF THE INVENTION

Styrene is one of the most important monomers in the modern petrochemical industry. It is used as a raw material in the production of many plastics, in particular polystyrene, as well as rubbers and resins. In 2006, United States consumption of styrene was about 14.4 billion pounds.

The most common method of production of styrene monomer (SM) is by dehydrogenation of ethylbenzene (EB). One process for production of styrene monomer from EB is by direct dehydrogenation. In this process, excess superheated steam near 800° C. is combined with EB in a low-pressure adiabatic reactor containing a potassium-promoted iron oxide catalyst. The reaction temperature is typically about 600 to 650° C. and the reaction pressure is typically about 40 to 80 kpa. The steam acts as a diluent to lower the partial pressure of the hydrogen by-product produced by the dehydrogenation reaction, allowing the reaction to proceed to a greater extent. The steam also provides the heat to drive the dehydrogenation reaction, which is highly endothermic, and decreases the amount of coke formation on the reactor catalyst by steam gasification. This process consumes high amounts of energy through the use of excess steam, and the energy required to vaporize and superheat the steam. It also has the disadvantages of catalyst deactivation and limited thermodynamic conversion.

The Lummus/UOP Smart Process is another process for conversion of EB to styrene that addresses some of the problems of direct dehydrogenation by using selective oxidation of a portion of the hydrogen by-product formed in the dehydrogenation reaction. The exothermic oxidation reaction of the hydrogen with oxygen provides at least part of the heat required for subsequent EB dehydrogenation. The removal of hydrogen from the process shifts the reaction equilibrium in the dehydrogenation unit to substantially increase single-pass EB conversions while maintaining high styrene monomer selectivity. Drawbacks of this process include the need for two catalysts in the reactor, one to catalyze the dehydrogenation reaction and a second catalyst for the oxidation of the hydrogen by oxygen. Reactor design and catalyst loading is more complicated in this system. Formation of aromatic oxidants in the reactor and $CO_2$ production can adversely affect the potassium-promoted iron oxide dehydrogenation catalyst. Also, there are safety concerns when injecting oxygen into a hydrocarbon mixture.

More recently, the use of $CO_2$ as a mild oxidant has been proposed. In a process described in U.S. Pat. No. 6,958,427, ethylbenzene is dehydrogenated to styrene monomer in the presence of carbon dioxide as a soft oxidant over a catalyst comprising vanadium and iron, with the $CO_2$ being externally supplied from the discharge of another petrochemical process. Compared with the conventional process, the presence of carbon dioxide allows operation at a lower temperature and provides enhanced conversion and significant energy savings. The use of $CO_2$ as an oxidant avoids the explosion risks of oxygen and shows high selectivity and conversion at lower temperatures than direct dehydrogenation. The $CO_2$ may also function as a heating medium and replace some or all of the steam used in conventional dehydrogenation processes.

The problems associated with this process are well known and described in U.S. Pat. No. 6,958,427, the entire contents of which are incorporated herein by reference. For example, drawbacks include high investment and operating cost due to the following: 1) the need for an externally supplied source of $CO_2$, such as the off-gas from an ethylene oxide plant; 2) the continued need for superheated steam as both a source of oxygen for "shifting" of by-product CO back to $CO_2$, and a source of at least part of the heat required for the endothermic reaction of EB to SM; 3) the need for a water/gas shift reactor; and 4) the need for separation of hydrogen from the water/gas shift reactor effluent; and/or 5) the need for separation of $CO_2$ from the dehydrogenation reactor off-gas, requiring an elaborate scrubbing/stripping operation; and 6) the need for a hydrogenation reactor (reverse water/gas shift reactor). The need for a continuous supply of $CO_2$ also limits the possible locations of the SM plant, since it must be located nearby a dedicated supply of $CO_2$. It is important to recognize that there is no net elimination of $CO_2$ by this process, despite claims that this is a "green" process. $CO_2$ is simply an oxygen carrier, which is converted to CO in the oxydehydrogenation reactor. The CO must be converted back to $CO_2$ by the water/gas shift reactor, or used to form some other oxygenated compounds.

The Oxirane POSM process produces SM as a co-product beginning with the oxidation of ethylbenzene to form ethylbenzene hydroperoxide intermediate, and subsequent epoxidation of propylene with the ethylbenzene hydroperoxide to yield equi-molar amounts of propylene oxide and styrene monomer. This process is extremely capital intensive and its economics are driven by the propylene oxide market.

In addition to the processes described above, the oxidative dehydrogenation of EB using oxygen as the oxidant, the Snamprogetti/Dow SNOW™ process (concurrent dehydrogenation of ethane and ethylbenzene), the Exelus ExSyM™ process (based on toluene and methanol feedstocks), a liquid-phase ethylbenzene dehydrogenation process (Pincer catalyst technology), and processes using membranes have been considered. These processes have not been demonstrated commercially.

It would be desirable to have a process for production of styrene by dehydrogenation of EB that avoids one or more of the drawbacks of prior dehydrogenation processes.

SUMMARY OF THE INVENTION

The present invention is directed generally to a process for the dehydrogenation of a functionally substituted aliphatic compound to form a functionally substituted aliphatic compound comprised of carbon-carbon double or triple bonds using recycled carbon dioxide. A recycle carbon dioxide feed stream and a stream containing a functionally substituted aliphatic compound are fed to a first oxydehydrogenation reactor containing at least one catalyst to convert functionally substituted aliphatic compound into a functionally substituted aliphatic compound comprised of carbon-carbon double or triple bonds. The effluent from the oxydehydrogenation reactor is separated into a gas recycle stream containing at least carbon dioxide, carbon monoxide, and hydrogen, a liquid dehydrogenation product mixture stream, and a water-rich stream. The gas recycle stream and an oxygen-containing stream are fed to at least one oxidizer to oxidize carbon monoxide and $H_2$ in the gas recycle stream to produce the recycle carbon dioxide stream and to heat the recycle carbon dioxide stream. The dehydrogenation product mixture stream is separated to obtain functionally substituted aliphatic compounds comprised of carbon-carbon double or triple bonds from the dehydrogenation product mixture.

In a preferred embodiment, the present invention is directed to processes for the production of styrene monomer (SM) by oxidative dehydrogenation (oxydehydrogenation) of ethylbenzene EB using carbon dioxide ($CO_2$) as a soft oxidant. The process of the present invention may also be used, for example, in processes wherein (1) the functionally substituted aliphatic compound in the feed is propane and the functionally substituted aliphatic product is propylene; (2) the functionally substituted aliphatic compound in the feed is butane and the functionally substituted aliphatic product is butene-1; (3) the functionally substituted aliphatic compound in the feed is butane and the functionally substituted aliphatic product is 1,3-butadiene; and (4) the functionally substituted aliphatic compound in the feed is butene-1 and the functionally substituted aliphatic product is 1,3-butadiene.

In the process for producing styrene from EB, in the dehydrogenation reactors, two parallel overall reactions for styrene monomer formation occur simultaneously: (1) direct EB dehydrogenation to styrene monomer over a catalyst using heat provided by the carbon dioxide, and (2) oxidative dehydrogenation of EB with carbon dioxide to form styrene monomer with water and carbon monoxide by-products.

The process of the present invention for producing styrene from EB is summarized below. One skilled in the art will readily appreciate that any of the functionally substituted aliphatic feed compounds described above may be substituted for EB in the feed to obtain the desired dehydrogenation product.

To produce styrene monomer, EB and recycled $CO_2$ are fed to a first dehydrogenation reactor containing a catalyst. Recycle gas is preheated in one or more heat exchangers and regenerated in one or more oxidizers. In the oxidizers, recycle gas is combined with oxygen over a catalyst to selectively oxidize carbon monoxide and hydrogen to produce carbon dioxide, steam and heat. The carbon monoxide and hydrogen are by-products of the oxidative dehydrogenation process. The EB is fed to the dehydrogenation reactors in vapor form.

The effluent from the first oxydehydrogenation reactor is reheated and fed to a second oxydehydrogenation reactor where further conversion of EB to styrene monomer occurs.

The effluent from the second oxydehydrogenation reactor may be used to preheat the recycle gas prior to regeneration. The reactor effluent is further cooled and partially condensed in a series of heat exchangers. The various condensed liquid streams are collected and separated into an organic phase (dehydrogenation product mixture) and an aqueous phase.

The dehydrogenation product mixture is fed to a series of distillation columns to separate the styrene monomer product from aromatic by-products of the dehydrogenation reaction and unreacted EB. The unreacted EB is fed back to the oxydehydrogenation reactors.

The aqueous phase is sent to a stripper for removal and recovery of dissolved hydrocarbons. The stripped condensate may be used as boiler feed water for steam generation.

The non-condensibles include CO, $CO_2$, $H_2$, $H_2O$ and $N_2$ (if air is used instead of oxygen in the oxidizers), and are saturated with aromatics. These constitute the reactor offgas. The reactor offgas is compressed and scrubbed with a poly-ethylbenzene stream to recover residual aromatics, producing a useful recycle gas. A small purge is taken to remove the net inflow of reaction inerts (e.g., $N_2$) from the recycle gas system. The recycle gas is then regenerated in the oxidizers, as described above.

Among the advantages of the present invention are that $CO_2$ has a high heat capacity and is safer to use in the process than oxygen. The use of carbon dioxide as an oxidant provides a higher expected conversion rate of EB to styrene and high selectivity for styrene. Based on thermodynamic equilibrium, lower reaction temperatures are required. Carbon dioxide is less expensive than superheated steam, and the carbon dioxide is not vaporized or condensed, which save the latent heat, saving energy costs. Furthermore, the process is a "green" process. That is, compared to other processes for producing styrene, it has less of an adverse impact on the environment. Other advantages of the process of the present invention will be apparent to those skilled in the art based upon the detailed description of embodiments of the invention set forth below.

DETAILED DESCRIPTION OF EMBODIMENTS OF THE INVENTION

Figure 1:
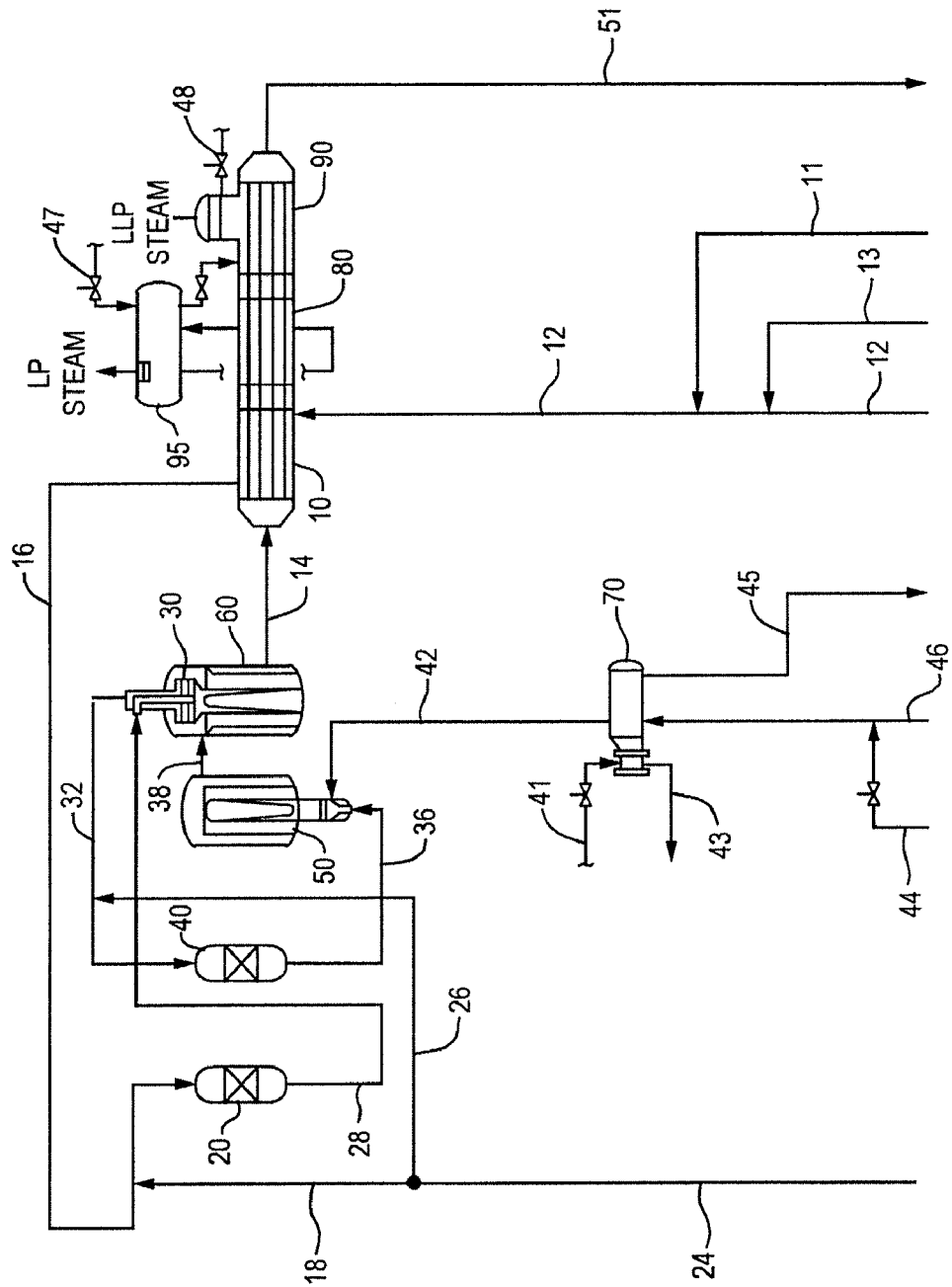
FIG. 1 shows a schematic of a plant for performing an embodiment of the process of the present invention for conversion of ethylbenzene to styrene monomer by oxidative dehydrogenation and the regeneration of recycle gas by oxidation of carbon monoxide and hydrogen.

The present invention is directed to an improved process for the dehydrogenation of a functionally substituted aliphatic compound to form a functionally substituted aliphatic compound comprised of carbon-carbon double or triple bonds using recycled carbon dioxide. A recycle carbon dioxide feed stream and a stream containing a functionally substituted aliphatic compound are fed to a first oxydehydrogenation reactor containing at least one catalyst to convert functionally substituted aliphatic compound into a functionally substituted aliphatic compound comprised of carbon-carbon double or triple bonds. The effluent from the oxydehydrogenation reactor is separated into a gas recycle stream containing at least carbon dioxide, carbon monoxide, and hydrogen, a liquid dehydrogenation product mixture stream, and a water-rich stream. The gas recycle stream and an oxygen-containing stream are fed to at least one oxidizer to oxidize carbon monoxide and $H_2$ in the gas recycle stream to produce the recycle carbon dioxide stream and to heat the recycle carbon dioxide stream. The dehydrogenation product mixture stream is separated to obtain functionally substituted aliphatic compounds comprised of carbon-carbon double or triple bonds from the dehydrogenation product mixture.

In one embodiment of the process of the present invention, styrene monomer (SM) is produced by oxydehydrogenation of ethylbenzene (EB). Carbon dioxide ($CO_2$) is used as a soft oxidant, as a diluent, and to provide heat for the conversion of ethylbenzene to styrene monomer. By-product carbon monoxide (CO) in the recycle gas is continuously regenerated by the oxidation to carbon dioxide, which is reused in the oxydehydrogenators. The oxidizers also convert by-product hydrogen ($H_2$) to steam, which is subsequently condensed and removed from the reaction system. Regeneration increases the enthalpy of the recycle gas and provides the net heat of reaction for oxydehydrogenation via sensible heat. Regenerated recycle gas also serves as reaction diluent.

Vaporized ethylbenzene is catalytically dehydrogenated to styrene in the presence of carbon dioxide, and a lesser amount of steam, in one or more adiabatic fixed bed radial reactors connected in series with reheating. By-product hydrogen is simultaneously oxidized by $CO_2$ (soft oxidation). Some side reactions occur in the oxydehydrogenators, notably dealkylation producing benzene and toluene. The dehydrogenation reaction is endothermic and the soft oxidation reaction is exothermic. The net reaction heat is provided by hot regenerated recycle gas, directly in the first oxydehydrogenator and indirectly in the second oxydehydrogenator.

Recycle gas, containing carbon monoxide, carbon dioxide, hydrogen, and other reaction by-products, is regenerated by the selective oxidation of carbon monoxide and hydrogen in one or more oxidizers in series. The oxidation of carbon monoxide to carbon dioxide produces the soft oxidant required by the oxydehydrogenation reactors. The oxidation of hydrogen to steam removes hydrogen, which limits EB conversion, from the oxydehydrogenation reaction system. The heats of combustion provide sensible heat to the recycle gas. The effluent from the first oxidizer is used to indirectly reheat the effluent from the first oxydehydrogenator (second oxydehydrogenator feed) in the recycle gas interchanger. The effluent from the second oxidizer is used to heat the feed to the first oxydehydrogenator by direct contact mixing at the oxydehydrogenator inlet.

Regenerated recycle gas, consisting mainly of carbon dioxide, is also used as a diluent in the oxydehydrogenation reactors to reduce the partial pressure of by-product hydrogen and to moderate the temperature drop in each of the oxydehydrogenators.

Ethylbenzene is catalytically dehydrogenated to styrene in the presence of carbon dioxide, and a lesser amount of steam, in one or more adiabatic fixed bed radial reactors connected in series with reheating. By-product hydrogen is simultaneously oxidized by $CO_2$ (soft oxidation).

EB is converted to styrene monomer in the one or more oxydehydrogenation reactors by two parallel reactions: (1) conventional EB dehydrogenation to styrene monomer by the following reaction:

$$EB \rightarrow Styrene + H_2;$$

and (2) oxidative dehydrogenation of EB to styrene monomer with carbon dioxide by the following reaction:

$$EB + CO_2 \rightarrow Styrene + CO + H_2O.$$

The second reaction can be thought of as the combination of the following two reactions:

$$EB \rightarrow SM + H_2 \quad \text{Conventional EB dehydrogenation} \tag{1}$$

$$H_2 + CO_2 \rightarrow CO + H_2O. \quad \text{Soft oxidation of } H_2 \tag{3}$$

The dehydrogenation reaction (1) is endothermic and the soft oxidation reaction (3) is exothermic. The soft oxidation reaction (3) serves to remove by-product hydrogen from the reaction gas mixture, which favorably changes the equilibrium conversion of the main EB dehydrogenation reaction (1). Exothermic reaction (3) also provides a portion of the heat required by endothermic reaction (1).

Some side reactions occur in the oxydehydrogenation reactors, notably dealkylation of EB producing benzene and toluene. These reactions can be written as follows:

$$EB + 2H_2 \rightarrow Benzene + 2\ Methane \tag{4}$$

$$EB + H_2 \rightarrow Toluene + Methane \tag{5}$$

Small amounts of other aromatic and aliphatic by-products can also be formed.

Recycle gas, containing carbon monoxide, carbon dioxide, hydrogen, and other reaction by-products, is regenerated by the selective oxidation of carbon monoxide and hydrogen in one or more oxidizers in series as follows:

$$\tfrac{1}{2}O_2 + CO \rightarrow CO_2 \quad CO_2\ \text{Regeneration} \tag{6}$$

$$\tfrac{1}{2}O_2 + H_2 \rightarrow H_2O \quad H_2\ \text{by-product removal} \tag{7}$$

Both oxidation reactions (6) and (7) are exothermic and provide the net heat for the oxidative dehydrogenation reactions (1) and (2). The first oxidation reaction (6) serves to remove the balance of by-product hydrogen from the recycle gas mixture, and further enhances the equilibrium conversion of the main EB dehydrogenation reaction (1). The net effects are operation at a lower temperature and/or higher per pass EB conversion. The second oxidation reaction serves to "regenerate" $CO_2$ (from CO), which is the oxidizing agent or "soft" oxidant used in the oxydehydrogenation reactors. Both oxidation reactions are highly exothermic and provide a large part of the heat required for the endothermic dehydrogenation reactions in the form of sensible heat. By-products from non-selective oxydehydrogenation reactions (e.g. methane) are also combusted in the oxidizers providing additional heat.

High or low purity oxygen, enriched air, or atmospheric air can be used as the oxygen feed to the oxidizers. Inert gases contained with the oxygen source are purged from the recycle gas to prevent their build-up to undesirable concentration.

Supplemental fuel (e.g., methane) is fed to the oxidizers and combusted to provide the initial inventory and any make-up requirements of $CO_2$. Supplemental fuel (e.g., methane or hydrogen) may also be fed to control the heat balance around the reactors, if required.

Multiple oxydehydrogenation reactors may be employed. The effluent from the first oxydehydrogenation reactor is reheated and fed to a second oxydehydrogenation reactor where further conversion of EB to styrene monomer occurs.

The effluent from the last oxydehydrogenation reactor may be used to preheat the recycle gas prior to regeneration. The reactor effluent is further cooled and partially condensed in a series of heat exchangers. The various condensed liquid streams are collected and separated into an organic phase (dehydrogenation product mixture) and an aqueous phase.

The dehydrogenation product mixture is fed to a series of distillation columns to separate the styrene monomer product from aromatic by-products of the dehydrogenation reaction and unreacted EB. The unconverted EB is combined with fresh EB feed and recycled to the oxydehydrogenation reactors.

The aqueous phase may be sent to a stripper for removal and recovery of dissolved hydrocarbons. The stripped condensate may be used as boiler feed water for steam generation.

The uncondensed reactor offgas, containing CO, $CO_2$, $H_2$, $H_2O$, $N_2$ (if air is used instead of oxygen in the oxidizers), small amounts of EB and SM, and small amounts of aliphatic and aromatic reaction by-product impurities, is compressed and scrubbed with a polyethylbenzene stream to recover residual aromatics.

A small recycle gas purge may be taken to remove the net inflow of reaction inerts (e.g., $N_2$) from the reaction system and to control the concentration to which they build up. If required, the purge may also be used to control the heat balance around the reactors by removing a portion of the combustible components (CO and $H_2$). The purge is taken after compression and scrubbing to minimize the loss of aromatics. The purge may be sent to flare or used as fuel gas.

The resulting recycle gas is then regenerated by oxidation of carbon monoxide and hydrogen, as described above.

The following detailed description of embodiments of the invention is intended to provide exemplary embodiments and is not intended to limit the full scope of the invention in any way.

Referring to FIG. 1, in one embodiment of the invention, a recycle gas stream (12) is fed to a recycle gas heater (10). The recycle gas stream (12) typically consists primarily of carbon dioxide and carbon monoxide, with some hydrogen and water and small amounts of aromatic and non-aromatic hydrocarbons. Preferably, the recycle gas stream (12) is fed at a pressure of between about 90 kPa and 110 kPa and at a temperature of between about 30° C. and 50° C.

Optionally, low pressure steam may be added to the recycle gas stream through line (11) or hydrogen or methane may be added through line (13). Supplemental methane or hydrogen is added upstream of the recycle gas heater to provide additional control of the heat and material balance in the recycle gas loop. Addition of methane or hydrogen can eliminate the need for make-up carbon dioxide. Low pressure steam may be used if desired to provide added heat to shift the dehydrogenation reactions in a favorable direction.

The recycle gas (12) is heated in the recycle gas heater (10) by heat exchange with the hot reactor effluent (14) described further below. The recycle gas exits the recycle gas heater (10) through line (16) and is fed to the first stage oxidizer (20). In the embodiment shown in FIG. 1, the recycle gas preferably exits the recycle gas heater (10) at a temperature of between about 400° C. and 500° C.

In the first stage oxidizer (20), the recycle gas is further heated by selective oxidation of a portion of the contained hydrogen, carbon monoxide and non-aromatic hydrocarbons using oxygen or air as the oxidizing agent. Any appropriate catalyst may be used in the oxidizer. Preferably, the first stage oxidizer uses a highly selective oxidation catalyst, such as UOP OC-5 catalyst. Oxygen is supplied through line (18) and may be mixed with the recycle gas prior to being fed to the first stage oxidizer. Alternatively, the oxygen and recycle gas may be fed separately to the first stage oxidizer. In the embodiment shown in FIG. 1, the oxygen is supplied through line (24) and split into two streams. The first stream flows through line (18) and is combined with the recycle gas to be fed to the first stage oxidizer, while the second stream flows through line (26) and is combined with the gas in line (32) to be fed to the second stage oxidizer as described below. Oxygen may be supplied as pure gas or in air. If desired, the oxygen may be preheated to a temperature of between about ambient and 30° C. The volume ratio of oxygen to recycle gas supplied to the first stage oxidizer is typically between about 0.030 and 0.035.

Optionally, a non-catalytic combustor may be used in place of the first stage oxidizer. However, this generally results in non-selective oxidation of all hydrocarbon components and resulting loss in yield.

The heated recycle gas is fed from the first stage oxidizer (20) through line (28) to the recycle gas interchanger (30). The heated recycle gas preferably exits the first stage oxidizer at a temperature of between about 700° C. and 800° C. The heated recycle gas is used to reheat the effluent from the first stage oxydehydrogenation reactor (50) which is fed to the recycle gas heat exchanger (30) through line (38). In alternative embodiments, it is possible to add any of the following between the first stage oxydehydrogenation reactor (50) and second stage oxydehydrogenation reactor (60) via an inlet line which intersect line (38) (not shown): $CO_2$, fuel, $O_2$/air, feed inlet stream and/or steam. As described below, the first stage oxydehydrogenation reactor effluent is reheated in the recycle gas interchanger (30) to reaction temperature before being fed to the second stage oxydehydrogenation reactor (40).

The recycle gas is fed from the recycle gas interchanger through line (32) to the second stage oxidizer (40). The temperature of the recycle gas exiting the recycle gas heat exchanger has been reduced by heat exchange, typically to a temperature of between about 550° C. and 650° C. Oxygen is provided through line (26) and may be mixed with the recycle gas prior to being fed to the second stage oxidizer. The oxygen may be supplied as air and may be preheated as described above. Optionally, the oxygen and recycle gas may be fed separately to the second stage oxidizer (40). Most of the remaining hydrogen, carbon monoxide and hydrocarbons in the recycle gas are selectively oxidized in the second stage oxidizer, providing additional heat for the process. The recycle gas is preferably heated in the second stage oxidizer to a temperature of between about 800° C. and 900° C. Any appropriate catalyst may be used in the oxidizer. Preferably, the second stage oxidizer uses a highly selective oxidation catalyst, such as UOP OC-5 type catalyst. The recycle gas exiting the second oxidizer is substantially free of hydrogen, carbon monoxide and non-aromatics produced in the dehydrogenation process as a result of the reactions in the two oxidizers.

Vaporized EB is fed through line (42) to the first stage oxydehydrogenation reactor (50) and mixed with the hot regenerated recycle gas (36) from the second stage oxidizer (40) which contains only very low amounts of hydrogen and carbon monoxide. Reactor (50) may be any hydrogenation reactor known in the art, including but not limited to a conventional dehydrogenation reactor, a UOP SMART reactor, a Lummus reactor and combinations of the same. The EB feed is vaporized in the EB vaporizer (70) at elevated pressure using high pressure steam as an indirect heat source. Steam is fed to the vaporizer through line (41) and condensate is removed through line (43). The EB vaporizer (70) is fed with recycled EB (46) from the distillation column for separating styrene monomer discussed further below and fresh EB (44) as required. As required, EB may be purged from the process through line (45) to remove heavy impurities contained in the recycle EB. The EB and regenerated recycle gas mixture is fed to the first stage oxydehydrogenation reactor at a temperature of between about 500° C. and 600° C.

The first stage oxydehydrogenation reactor may be any type of reactor typically used in dehydrogenation processes. The reactor may include one or more fixed beds, one or more fluidized beds, or a combination of these types of beds. The catalyst used in the reactor may be any catalyst appropriate for the oxydehydrogenation of EB in the presence of carbon dioxide, such as a potassium-promoted iron oxide catalyst, vanadium and iron catalyst, or other catalyst.

A portion of the EB is converted to styrene monomer in the first stage oxydehydrogenation reactor (50). The effluent from the first stage oxydehydrogenation reactor (50) is fed through line (38) to the recycle gas interchanger (30) where it is heated to reaction temperature of between about 550° C. and 600° C. by heat exchange with the recycle gas as previously described. After being heated to reaction temperature in the recycle gas interchanger, the effluent is fed to the second stage oxydehydrogenation reactor (60). The second stage oxydehydrogenation reactor is also any type of reactor typically used in dehydrogenation processes, and may include one or more fixed beds, one or more fluidized beds, or a combination of these types of beds. The catalyst used in the reactor may be any catalyst appropriate for the oxydehydrogenation of EB in the presence of carbon dioxide, such as a potassium-promoted iron oxide catalyst, vanadium and iron catalyst, or other catalyst.

The effluent from the second stage oxydehydrogenation reactor is a dehydrogenation mixture comprising styrene monomer, unreacted EB, carbon dioxide, and byproducts such as hydrogen, carbon monoxide and aromatic and aliphatic hydrocarbons. The dehydrogenation mixture is fed through line (14) to the recycle gas heater (10) where it is cooled by heat exchange with the recycle gas as previously described. Additional cooling of the dehydrogenation mixture from the second stage oxydehydrogenation reactor takes place in the low pressure waste heat exchanger (80) and the low pressure waste heat exchanger (90) using cooling water (47, 48) in a similar manner as in a conventional EB conversion process. A steam drum (95) may be included as part of the cooling equipment. The dehydrogenation mixture is typically cooled to a temperature of between about 100° C. and 150° C. in the waste heat exchangers.

Figure 2:
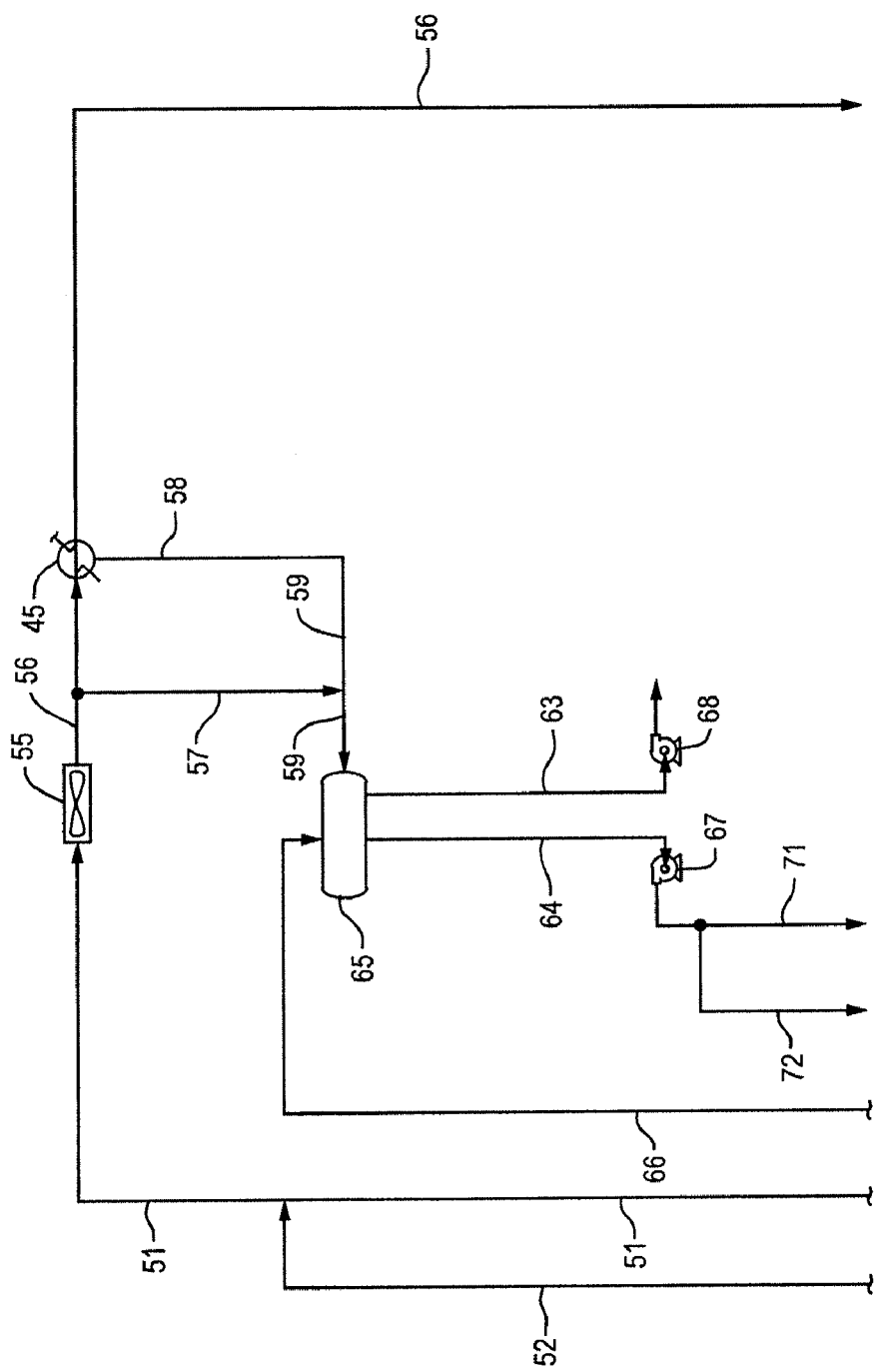
FIG. 2 shows a schematic of a plant for separating the reactor effluent into dehydrogenation product mixture, an aqueous stream, and reactor offgas.

The cooled dehydrogenation mixture is fed through line (51) for further processing to separate the styrene monomer from the other components of the dehydrogenation mixture. This separation can be performed using conventional techniques for separation of styrene monomer from dehydrogenation mixtures. In one embodiment of the process shown in FIG. 2, the dehydrogenation mixture is further cooled in main condenser (55) and trim condenser (95). Approximately half of the water and aromatics are condensed in the condensers. Water and aromatics condensed in the main condenser are removed through line (56) prior to feeding the mixture to the trim condenser, and water and aromatics condensed in the trim condenser are removed through line (58). The condensed water and aromatics are fed through line (59) to a dehydrogenation mixture/water separator (65). Condensed water and hydrocarbons are separated in the dehydrogenation/water separator.

The dehydrogenation mixture is pumped from the separator (65) through line (64) using pump (67). The dehydrogenated mixture may be fed through line (71) to a distillation section to separate styrene monomer from residual EB and other byproducts. The distillation section operates in the same manner as in a conventional EB conversion process. EB recovered in the distillation section is recycled and fed to the dehydrogenation reactors as discussed above. If desired, some or all of the dehydrogenation mixture may be fed through line (72) for storage.

Water from the separator (65) is pumped through line (63) and is processed through a stripper (105) along with other process condensate streams for removal and recovery of hydrocarbons. The condensate stripper portion of the process operates in the same manner as a conventional process for EB dehydrogenation to styrene monomer.

Figure 3:
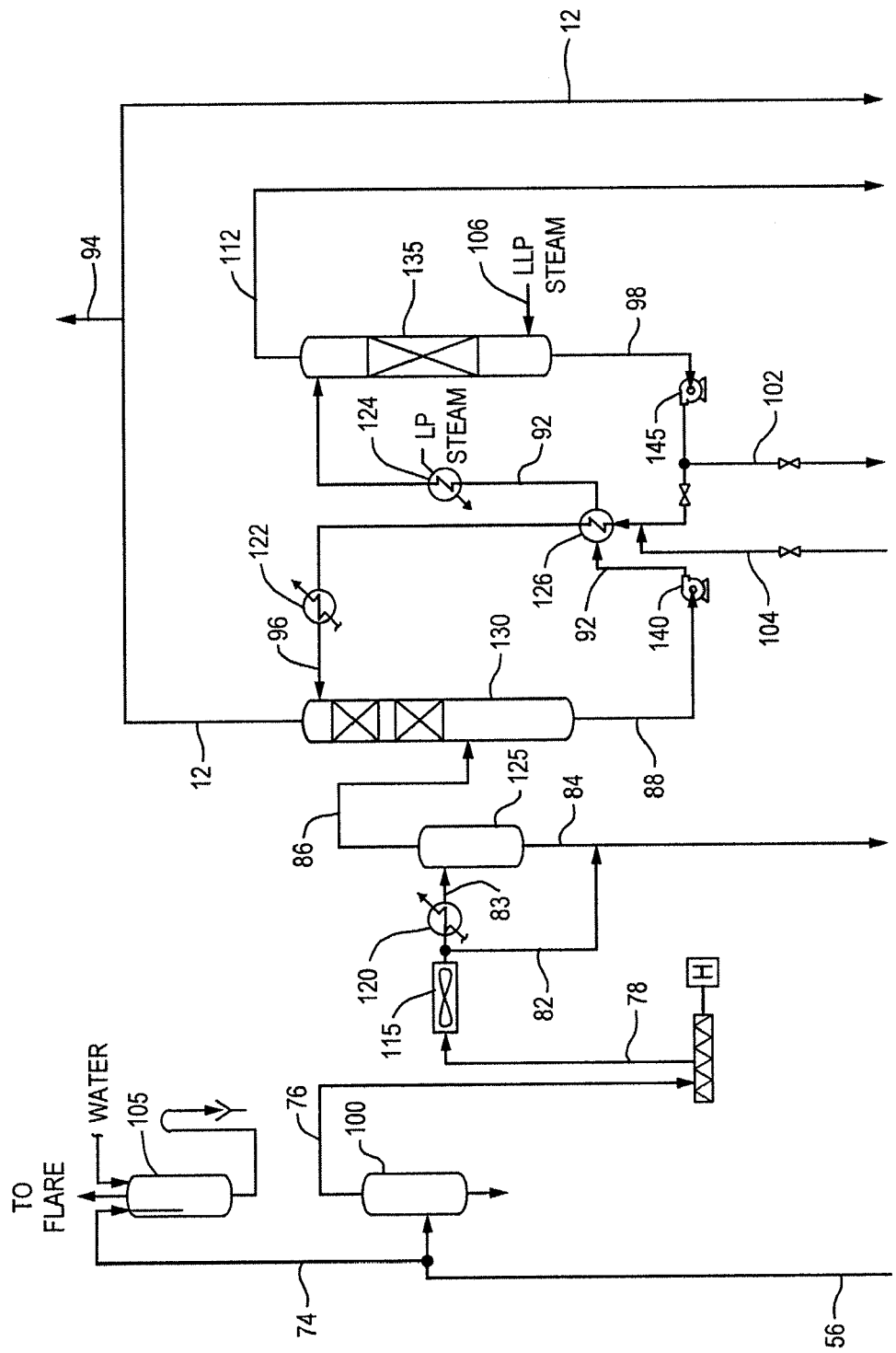
FIG. 3 shows a schematic of a plant for compressing and scrubbing the reactor offgas to recover aromatics and produce a useful recycle gas.

Cooled recycle gas exits in line (56). Because the process of the present invention results in a lower water concentration in the effluent than in a conventional EB conversion process, the gas is not desuperheated with process water. The recycle gas is processed as shown in FIG. 3. The recycle gas flows through line (56) to recycle gas compressor suction drum (100). A line (74) allows recycle gas to flow to recycle gas relief drum (105) if necessary. The recycle gas flows through compressor inlet line (76) to compressor (110), where the gas is compressed to the pressure required for processing and plant operation. The compressed recycle gas flows through outlet line (78) to the recycle gas cooler (15) and trim cooler (120), where most of the remaining water and aromatics are condensed. The condensed water and aromatic hydrocarbons are fed through line (83) to a separator (125) and the condensed water and aromatics are removed through lines (82) and (84). No water is injected into the gas coolers.

The cooled compressed recycle gas is fed from the separator (125) through line (86) to flux oil scrubber (130). The recycle gas is scrubbed in a flux oil scrubber where cooled lean flux oil (96) is used to absorb substantially all of any remaining aromatics from the recycle gas. The recycle gas flows through line (12). The recycle gas is purged to remove any gases such as nitrogen or argon that may have entered the system with the oxygen feed. The purge is taken after scrubbing to minimize aromatic losses with the purge. If air is used to supply oxygen to the system, a larger purge flow is needed and make-up carbon dioxide may need to be supplied. The scrubbed recycle gas, essentially free of aromatics, is fed through line (12) to the recycle gas heater (10) as described above.

The bottoms from the flux oil scrubber are removed through line (88) using pump (140) and fed through line (92) to flux oil stripper (135). The flux oil stripper is used to recover hydrocarbons from the rich flux oil. The overhead from the flux oil stripper (112) is fed to a condenser to recover hydrocarbons. The bottoms (98) from the flux oil stripper contain lean flux oil that is fed using pump (145) to the flux oil scrubber (130). Low pressure steam is provided to the flux oil stripper through line (106).

Heat exchangers may be used to control the temperature of the flux oil and the feed to the flux oil stripper. For example, heat exchanger (126) may be provided to preheat the bottoms (88) from the flux oil scrubber prior to feed to the flux oil stripper. The feed to the flux oil stripper may be further heated using steam in heat exchanger (124). The flux oil feed to the flux oil scrubber may be further cooled using water in heat exchanger (122).

Make up flux oil may be provided through line (104) while blowdowm may be removed through line (102).

Process condensate is sent to the process condensate stripper for removal and recovery of hydrocarbons. The stripped condensate is reused in the plant steam system. This system operates in a similar manner as in prior EB conversion processes.

Some of the carbon monoxide and carbon dioxide contained in the recycle gas system may be lost in the recycle gas purge. Carbon dioxide make-up can be supplied externally or produced in situ by the oxidation of methane or other light hydrocarbon.

One advantage of the process is that the low hydrogen concentrations at the inlet of the first stage oxydehydrogenation reactor and the simultaneous soft oxidation of by-product hydrogen in the oxydehydrogenation reactors allows the conversion reactions to proceed more favorably. As a result, the oxydehydrogenation reactors may be operated at approximately 50° C. below the temperature of reactors in a conventional EB conversion plant.

While preferred embodiments have been shown and described, various modifications may be made to the processes described above without departing from the spirit and scope of the invention as described in the appended claims. Accordingly, it is to be understood that the present invention has been described by way of example and not by limitation.

We claim:
1. A process for the dehydrogenation of a functionally substituted aliphatic compound to form a functionally substi- tuted aliphatic compound comprised of carbon-carbon double or triple bonds using recycled carbon dioxide comprising the steps of:
(a) feeding a recycle carbon dioxide stream and a stream containing a functionally substituted aliphatic compound to a first oxydehydrogenation reactor containing at least one catalyst to convert functionally substituted aliphatic compound into a functionally substituted aliphatic compound comprised of carbon-carbon double or triple bonds;
(b) separating the effluent from the oxydehydrogenation reactor into a gas recycle stream containing at least carbon dioxide, carbon monoxide, and hydrogen, a liquid dehydrogenation product mixture stream, and a water-rich stream;
(c) feeding the gas recycle stream containing at least carbon dioxide, carbon monoxide and hydrogen and an oxygen-containing stream to at least one oxidizer to oxidize carbon monoxide and $H_2$ in the gas recycle stream to produce the recycle carbon dioxide stream and to heat the recycle carbon dioxide stream;
(d) separating the dehydrogenation product mixture stream to separate functionally substituted aliphatic compound comprised of carbon-carbon double or triple bonds from the dehydrogenation product mixture; wherein the functionally substituted aliphatic compound in the feed stream is ethylbenzene and the functionally substituted aliphatic product is styrene monomer.

2. The process of claim 1, further comprising the step of reheating said oxydehydrogenation reactor effluent in a heat exchanger and feeding said effluent to a oxydehydrogenation reactor containing at least one catalyst.

3. The process of claim 1, wherein the water-rich stream is further processed to reduce the hydrocarbons in the water-rich stream.

4. The process of claim 1, wherein the dehydrogenation product mixture is separated from the gas stream containing $CO_2$, CO, and $H_2$ by cooling or compression.

5. The process of claim 3, wherein the dehydrogenation product mixture is further separated from the gas stream containing $CO_2$, CO, and $H_2$ by scrubbing the gas stream with a low-volatility hydrocarbon liquid.

6. The process of claim 4, wherein the dehydrogenation product mixture is separated from the low-volatility hydrocarbon liquid by stripping.

7. The process of claim 1, wherein the oxygen-containing stream is air.

8. The process of claim 1, wherein the oxygen-containing stream is enriched in oxygen.

9. The process of claim 1, wherein the oxygen-containing stream is more than 98 mol % oxygen.

10. The process of claim 1, wherein the at least one oxidizer contains at least one catalyst.

11. The process of claim 10, wherein the at least one oxidizer contains at least one catalyst that preferentially promotes reaction of oxygen with CO and $H_2$ and does not substantially promote reaction of oxygen with hydrocarbons in the gas recycle stream.

12. The process of claim 1, wherein there are two oxidizers and two dehydrogenator reactors with one reheater between them.

13. The process of claim 1, further comprising the step of adding steam to the recycled carbon dioxide stream.

14. The process of claim 1, further comprising the step of adding at least one of hydrogen, methane, or other hydrocarbon fuel to the recycle carbon dioxide stream.

15. A process for dehydrogenation of ethylbenzene to form styrene monomer using carbon dioxide comprising the steps of:
(a) providing a carbon dioxide stream wherein the carbon dioxide stream comprises carbon dioxide recycled from at least one dehydrogenation reactor;
(b) heating at least one of the carbon dioxide stream and the EB in a heat exchanger;
(c) feeding the carbon dioxide stream and an oxygen stream to a first oxidizer having a selective oxidation catalyst to catalyze oxidation of dehydrogenation by-products contained in the recycled carbon dioxide;
(d) feeding the effluent stream from the first oxidizer to a recycle gas heat exchanger to heat the effluent from a first dehydrogenation reactor and cool the effluent stream from the first oxidizer;
(e) feeding the cooled effluent stream from the first oxidizer and an oxygen stream to a second oxidizer having a selective oxidation catalyst to catalyze oxidation of dehydrogenation by-products contained in the recycled carbon dioxide;
(f) feeding the effluent from the second oxidizer and ethylbenzene to a first dehydrogenation reactor containing a catalyst to catalyze dehydrogenation of ethylbenzene to styrene;
(g) feeding the effluent from the first dehydrogenation reactor to the recycle gas heat exchanger to heat the effluent from the first dehydrogenation reactor;
(h) feeding the heated first dehydrogenation reactor effluent from the recycle gas heat exchanger to a second dehydrogenation reactor containing a catalyst to catalyze dehydrogenation of ethylbenzene to styrene;
(i) separating the effluent from the second dehydrogenation reactor into the recycle carbon dioxide stream and a dehydrogenation product mixture stream; and
(j) feeding the dehydrogenation product mixture stream to a distillation column to separate styrene monomer from the dehydrogenation product mixture.

* * * * *